United States Patent [19]

Goelz et al.

[11] Patent Number: 5,545,723
[45] Date of Patent: Aug. 13, 1996

[54] MUTEINS OF IFN-β

[75] Inventors: Susan E. Goelz, Winchester; Richard L. Cate, Cambridge; E. Pingchang Chow, Charlestown; R. Blake Pepinsky, Watertown, all of Mass.

[73] Assignee: Biogen Inc., Cambridge, Mass.

[21] Appl. No.: 213,448

[22] Filed: Mar. 15, 1994

[51] Int. Cl.⁶ .......................... C12N 15/22; C07K 14/565
[52] U.S. Cl. ................. 424/85.6; 424/85.6; 536/23.52; 514/12; 435/69.51; 435/320.1; 435/252.3; 530/351
[58] Field of Search ................. 530/351; 424/85.6; 536/23.52; 435/69.51, 320.1, 252.3; 514/12

[56] References Cited

U.S. PATENT DOCUMENTS

| | | | |
|---|---|---|---|
| Re. 33,653 | 7/1991 | Mark et al. ............... | 424/85.1 |
| 4,518,584 | 5/1985 | Mark et al. . | |
| 4,530,787 | 7/1985 | Shaked et al. . | |
| 4,572,798 | 2/1986 | Koths et al. . | |
| 4,588,585 | 5/1986 | Mark et al. . | |
| 4,737,462 | 4/1988 | Mark et al. . | |
| 4,738,844 | 4/1988 | Bell et al. . | |
| 4,738,845 | 4/1988 | Bell et al. ............... | 424/85.6 |
| 4,751,077 | 6/1988 | Bell et al. ............... | 424/85.6 |
| 4,753,795 | 6/1988 | Bell et al. . | |
| 4,769,233 | 9/1988 | Bell et al. . | |
| 4,793,995 | 12/1988 | Bell et al. . | |
| 4,816,440 | 3/1989 | Thomson . | |
| 4,853,332 | 8/1989 | Mark et al. . | |
| 4,914,033 | 4/1990 | Bell et al. . | |
| 4,959,314 | 9/1990 | Mark et al. . | |
| 4,992,271 | 2/1991 | Fernandes et al. . | |
| 5,183,746 | 2/1993 | Shaked et al. ............. | 435/69.51 |

FOREIGN PATENT DOCUMENTS

| | | |
|---|---|---|
| 109748 | 5/1984 | European Pat. Off. . |
| 131816 | 1/1985 | European Pat. Off. . |
| 130566 | 1/1985 | European Pat. Off. . |
| 130565 | 1/1985 | European Pat. Off. . |
| 218825 | 4/1987 | European Pat. Off. . |
| 260350 | 3/1988 | European Pat. Off. . |
| 372707 | 6/1990 | European Pat. Off. . |
| 041313 | 9/1990 | European Pat. Off. . |
| 2130219 | 1/1986 | United Kingdom . |
| 2168055 | 6/1986 | United Kingdom . |

OTHER PUBLICATIONS

Berthold, Wolfgang, et al., *European Journal of Biochemistry*, vol. 87, 367–370 (1978).
Borukhov, Sergey I., et al., *Biochemical and Biophysical Research Communications*, vol. 167, No. 1, 74–80 (1990).
Khosrovi, Bezhad, *Interferon: Research, Clinical Application, and Regulatory Consideration*, Proceedings of an International Workshop, 89–99 (1983).
Mark, D. F., et al., *Proceedings of National Academy of Science USA*, vol. 81, 5662–5666 (1984).
Otto, Michael J., et al., *Journal Of Virology*, vo. 35, No. 2, 390–399 (1980).
Shepard, H. Michael, et al., *Nature*, vol. 294, No. 5841, 563–565 (1981).
Stewart, A. G., et al., *DNA—A Journal of Molecular Biology*, vol. 6, No. 2, 119–128 (1987).

*Primary Examiner*—Garnette D. Draper
*Assistant Examiner*—Shelly Guest Cermak
*Attorney, Agent, or Firm*—Fish & Neave; James F. Haley, Jr.; Ivor R. Elrifi

[57] ABSTRACT

A IFN-β mutein in which phe (F), tyr (Y), trp (W) or his (H) is substituted for val (V) at position 101, when numbered in accordance with wild type IFN-β, DNA sequences encoding these IFN-β muteins, recombinant DNA molecules containing those DNA sequences operatively linked to expression control sequences and capable of inducing expression of an IFN-β mutein, hosts transformed with those recombinant DNA molecules, pharmaceutical compositions containing IFN-β muteins and methods of using those compositions to treat viral infections, cancer or tumors or for immunomodulation.

15 Claims, 4 Drawing Sheets

```
  1 MSYNLLGFLQ RSSNFQCQKL  20
 21 LWQLNGRLEY CLKDRMNFDI  40
 41 PEEIKQLQQF QKEDAALTIY  60
 61 EMLQNIFAIF RQDSSTGWNY  80
 81 ETIVENLLAN VYHQINHLKT 100
101 FLEEKLEKED FTRGKLMSSL 120
121 HLKRYYGRIL HYLKAKEYSH 140
141 CAWTIVRVEI LRNFYFINRL 160
161 TGYLRN
```

FIG. 1

```
        -20              -15              -10               -5
ATGACCAACAAGTGTCTCCTCCAAATTGCTCTCCTGTTGTGCTTCTCCACTACAGCT
 M  T  N  K  C  L  L  Q  I  A  L  L  L  C  F  S  T  T  A 1                5               10               15
CTTTCCATGAGCTACAACTTGCTTGGATTCCTACAAAGAAGCAGCAATTTTCAGTGT
 L  S  M  S  Y  N  L  L  G  F  L  Q  R  S  S  N  F  Q  C 20               25               30               35
CAGAAGCTCCTGTGGCAATTGAATGGGAGGCTTGAATACTGCCTCAAGGACAGGATG
 Q  K  L  L  W  Q  L  N  G  R  L  E  Y  C  L  K  D  R  M 40               45               50               55
AACTTTGACATCCCTGAGGAGATTAAGCAGCTGCAGCAGTTCCAGAAGGAGGACGCC
 N  F  D  I  P  E  E  I  K  Q  L  Q  Q  F  Q  K  E  D  A 60               65               70
GCATTGACCATCTATGAGATGCTCCAGAACATCTTTGCTATTTTCAGACAAGATTCA
 A  L  T  I  Y  E  M  L  Q  N  I  F  A  I  F  R  Q  D  S 75               80               85               90
TCTAGCACTGGCTGGAATGAGACTATTGTTGAGAACCTCCTGGCTAATGTCTATCAT
 S  S  T  G  W  N  E  T  I  V  E  N  L  L  A  N  V  Y  H 95              100              105              110
CAGATAAACCATCTGAAGACATTCCTGGAAGAAAAACTGGAGAAAGAAGATTTCACC
 Q  I  N  H  L  K  T  F  L  E  E  K  L  E  K  E  D  F  T 115              120              125              130
AGGGGAAAACTCATGAGCAGTCTGCACCTGAAAAGATATTATGGGAGGATTCTGCAT
 R  G  K  L  M  S  S  L  H  L  K  R  Y  Y  G  R  I  L  H 135              140              145              150
TACCTGAAGGCCAAGGAGTACAGTCACTGTGCCTGGACCATAGTCAGAGTGGAAATC
 Y  L  K  A  K  E  Y  S  H  C  A  W  T  I  V  R  V  E  I 155              160              165
CTAAGGAACTTTTACTTCATTAACAGACTTACAGGTTACCTCCGAAAC
 L  R  N  F  Y  F  I  N  R  L  T  G  Y  L  R  N
```

FIG. 2

MUTEINS OF IFN-β

TECHNICAL FIELD OF THE INVENTION

This invention relates to muteins of interferon-beta ("IFN-β") in which val (V) at position 101, when numbered in accordance with wild type IFN-β, is substituted with phe (F), trp (W), tyr (Y) or his (H).

BACKGROUND OF THE INVENTION

Interferons are single chain polypeptides secreted by most animal cells in response to a variety of inducers, including viruses, mitogens and polynucleotides. Interferons participate in regulation of cell function, and have antiviral, antiproliferative and immunomodulating properties. Native-human interferons are classified into three major types: α-IFN (leukocyte), IFN-β (fibroblast) and γ-IFN (immune). Native IFN-β is produced primarily by diploid fibroblast cells and in lesser amounts by lymphoblastoid cells.

IFN-β is a glycoprotein. Its nucleic acid and amino acid sequences have been determined. (Houghton et al., "The Complete Amino Acid Sequence of Human Fibroblast Interferon as Deduced Using Synthetic Oligodeoxyribonucleotide Primers of Reverse Transcriptase," *Nucleic Acids Research*, 8, pp. 2885–94 (1980); T. Taniguchi et al., "The Nucleotide Sequence of Human Fibroblast DNA," *Gene*, 10, pp. 11–15 (1980)). Recombinant IFN-β has been produced and characterized.

IFN-β exhibits various biological and immunological activities. One of IFN-β's biological activities is its antiviral activity. This antiviral activity can be neutralized by antibodies to IFN-β. See EP-B1-41313. Preparation and purification of antibodies to IFN-β is described in EP-B1-41313 and the references cited therein. IFN-β is also able to bind to cells that express interferon receptors, such as Daudi cells or A549 cells.

As a result of these activities, IFN-β has potential applications in immunotherapy, antitumor and anticancer therapies, and antiviral therapies.

Numerous investigations and clinical trials have been and continue to be conducted into the antitumor and anticancer properties of both wild type and recombinant IFN-β. These include treatment of several malignant diseases such as osteosarcoma, basal cell carcinoma, cervical dysplasia, glioma, acute myeloid leukemia, multiple myeloma and Hodgkin's disease. In addition, IFN-β has been shown to cause local tumor regression when injected into subcutaneous tumoral nodules in melanoma and breast carcinoma-affected patients.

IFN-β (wild-type and recombinant) has been tested clinically in a variety of viral infections, including papilloma viruses, such as genital warts and condylomata of the uterine cervix; viral hepatitis, including acute/chronic hepatitis B and non-A, non-B hepatitis (hepatitis C); herpes genitalis; herpes zoster; herpetic keratitis; herpes simplex; viral encephalitis; cytomegalovirus pneumonia; and in the prophylaxis of rhinovirus.

Clinical trials using recombinant IFN-β in the treatment of multiple sclerosis have also been conducted and IFN-β is approved for sale in the United States for the treatment of multiple sclerosis.

SUMMARY OF THE INVENTION

This invention provides muteins of IFN-β wherein the val (V) at position 101, when numbered in accordance with wild type IFN-β, is substituted with phe (F), tyr (Y), trp (W), or his (H). This invention also provides DNA sequences encoding these IFN-β muteins, recombinant DNA molecules containing those sequences operatively linked to expression control sequences and capable of inducing, in an appropriate host, the expression of the IFN-β muteins, hosts transformed with those recombinant DNA molecules and pharmaceutical compositions containing the IFN-β. These compositions are useful in immunotherapy as well as in anticancer, antitumor and antiviral therapies.

BRIEF DESCRIPTION OF THE DRAWINGS

FIG. 1 depicts the amino acid sequence of the preferred mutein of this invention IFN-β(phe$_{101}$) (SEQ ID NO: 1).

FIG. 2 depicts the preferred degenerate DNA sequence encoding IFN-β(phe$_{101}$) and the signal sequence of native IFN-β (SEQ ID NO: 2).

DETAILED DESCRIPTION OF THE INVENTION

Figure 3A:
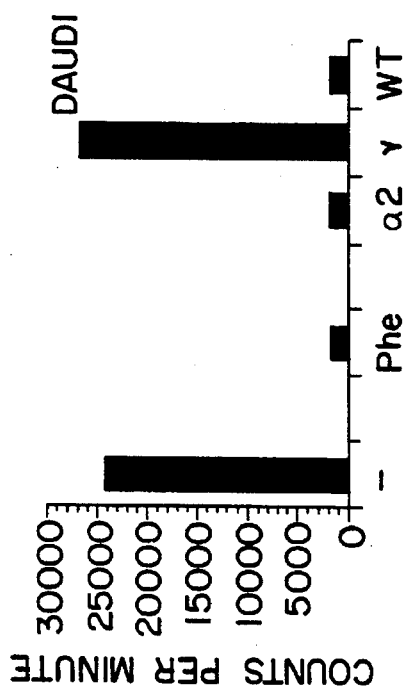
FIGS. 3(A–D) shows an analysis of IFN-β(phe$_{101}$) binding to interferon receptor bearing cells. Panel A shows receptor binding data for $^{125}$I-IFN-β(phe$_{101}$) to Daudi cells. Panel B shows receptor binding data for wild type $^{125}$I-IFN-β to Daudi cells. Panel C shows receptor binding data for $^{125}$I-IFN-β(phe$_{101}$) to A549 cells. Panel D shows receptor binding data for wild type $^{125}$I-IFN-β to A549 cells.
Figure 3C:
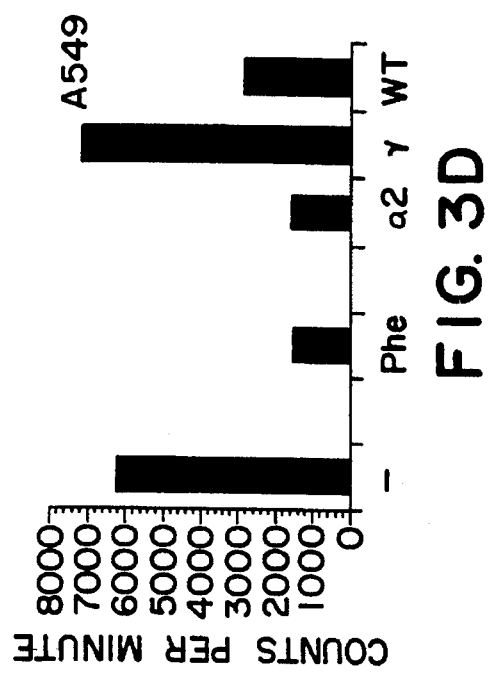
Figure 3B:
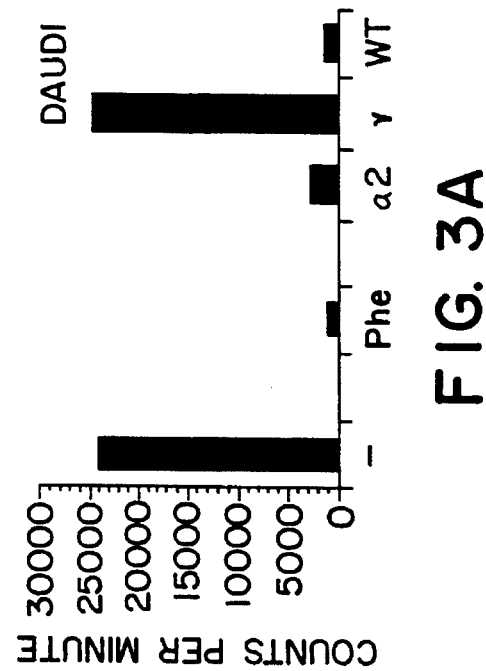
Figure 3D:
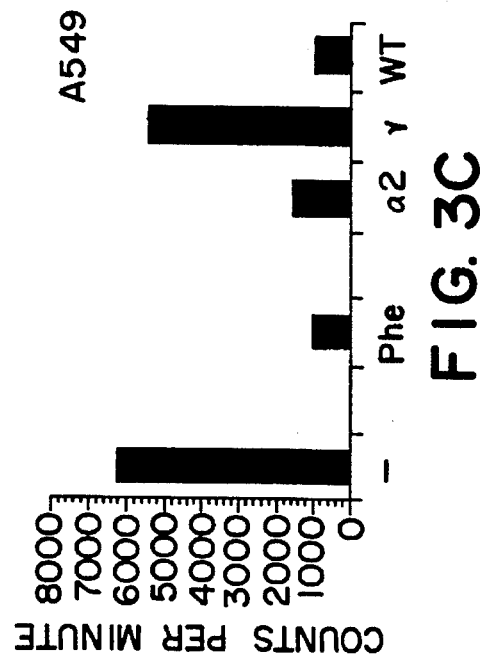
Figure 4A:
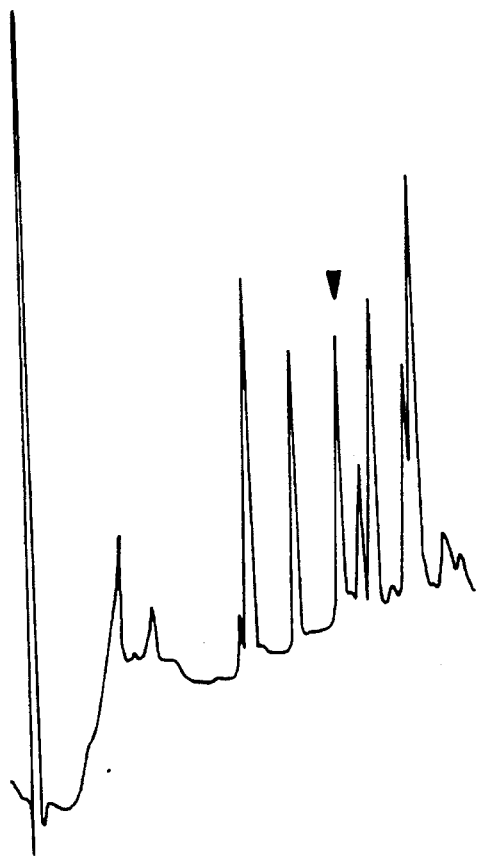
FIGS. 4A+B show an analysis of IFN-β (phe$_{101}$) and wild type IFN-β by peptide mapping by endoproteinase Lyse-C.
Figure 4B:
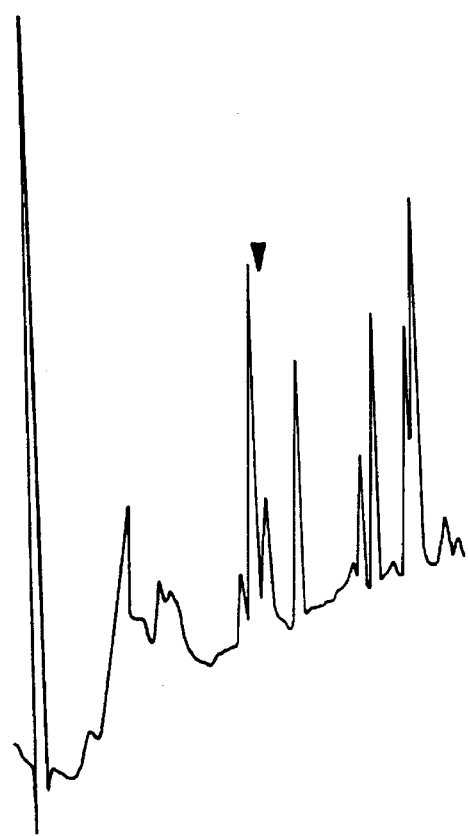

As used herein, "wild type IFN-β" means an IFN-β, whether native or recombinant, having the normally occurring amino acid sequence of native human IFN-β, as shown, e.g., in EP-B1-41313, FIG. 4.

As used herein, "IFN-β mutein" means a polypeptide wherein the val (V) at position 101, when numbered in accordance with wild type IFN-β, is substituted with phe (F), tyr (Y), trp (W), or his (H), preferably phe (F). Our most preferred IFN-β muteins have an amino acid sequence identical to wild type IFN-β at the other residues. However, the IFN-β muteins of this invention may also be characterized by amino acid insertions, deletions, substitutions and modifications at one or more sites in or at the other residues of the native IFN-β polypeptide chain. In accordance with this invention any such insertions, deletions, substitutions and modifications result in an IFN-β mutein that retains an antiviral activity that can be at least partially neutralized by antibodies to wild type IFN-β.

We prefer conservative modifications and substitutions (i.e., those that have a minimal effect on the secondary or tertiary structure of the mutein). Such conservative substitutions include those described by Dayhoff in the *Atlas of Protein Sequence and Structure*, 5 (1978), and by Argos in *EMBO J.*, 8, 779–785 (1989). For example, amino acids belonging to one of the following groups represent conservative changes:

ala, pro, gly, gln, asn, ser, thr;

cys, ser, tyr, thr;

val, ile, leu, met, ala, phe;

lys, arg, his; and phe, tyr, trp, his.

We also prefer modifications or substitutions that eliminate sites for intermolecular crosslinking or incorrect disulfide bond formation. For example, IFN-8 is known to have three cys residues, at wild-type positions 17, 31 and 141.

U.S. Pat. No. 4,588,585 refers to an IFN-β mutein in which the cys (C) at position 17 has been substituted with ser (S). This substitution can also be utilized in this invention. For example, this invention contemplates an IFN-β mutein having ser (S) substituted for cys (C) at position 17 and val (V) at position 101 substituted with phe (F), trp (W), tyr (Y), or his (H), preferably phe (F), when numbered in accordance with wild type IFN-β.

By "numbered in accordance with wild type IFN-β" we mean identifying a chosen amino acid with reference to the position at which that amino acid normally occurs in wild type IFN-β. Where insertions or deletions are made to the IFN-β mutein, one of skill in the art will appreciate that the val (V) normally occurring at position 101, when numbered in accordance with wild type IFN-β, may be shifted in position in the mutein. However, the location of the shifted val (V) can be readily determined by inspection and correlation of the flanking amino acids with those flanking $val_{101}$ in wild type IFN-β.

The IFN-β muteins of the present invention can be produced by any suitable method known in the art. Such methods include constructing a DNA sequence encoding the IFN-β muteins of this invention and expressing those sequences in a suitable transformed host. This method will produce recombinant muteins of this invention. However, the muteins of this invention may also be produced, albeit less preferably, by chemical synthesis or a combination of chemical synthesis and recombinant DNA technology.

In one embodiment of a recombinant method for producing a mutein of this invention, a DNA sequence is constructed by isolating or synthesizing a DNA sequence encoding the wild type IFN-β and then changing the codon for $val_{101}$ to a codon for phe (F), trp (W), tyr (Y) or his (H), preferably phe (F), by site-specific mutagenesis. This technique is well known. See, e.g., Mark et al., "Site-specific Mutagenesis Of The Human Fibroblast Interferon Gene", *Proc. Natl. Acad. Sci. USA*, 81, pp. 5662–66 (1984); U.S. Pat. No. 4,588,585, incorporated herein by reference.

Another method of constructing a DNA sequence encoding the IFN-β muteins of this invention would be chemical synthesis. For example, a gene which encodes the desired IFN-β mutein may be synthesized by chemical means using an oligonucleotide synthesizer. Such oligonucleotides are designed based on the amino acid sequence of the desired IFN-β mutein, and preferably selecting those codons that are favored in the host cell in which the recombinant mutein will be produced. In this regard, it is well recognized that the genetic code is degenerate—that an amino acid may be coded for by more than one codon. For example, phe (F) is coded for by two codons, TTC or TTT, tyr (Y) is coded for by TAC or TAT and his (H) is coded for by CAC or CAT. Trp (W) is coded for by a single codon, TGG. Accordingly, it will be appreciated that for a given DNA sequence encoding a particular IFN-β mutein, there will be many DNA degenerate sequences that will code for that IFN-β mutein. For example, it will be appreciated that in addition to the preferred DNA sequence shown in FIG. 2, there will be many degenerate DNA sequences that code for the IFN-β mutein shown in FIG. 1. These degenerate DNA sequences are considered within the scope of this invention.

The DNA sequence encoding the IFN-β mutein of this invention, whether prepared by site directed mutagenesis, synthesis or other methods, may or may not also include DNA sequences that encode a signal sequence. Such signal sequence, if present, should be one recognized by the cell chosen for expression of the IFN-β mutein. It may be prokaryotic, eukaryotic or a combination of the two. It may also be the signal sequence of native IFN-β. The inclusion of a signal sequence depends on whether it is desired to secrete the IFN-β mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IFN-β signal sequence be used.

Standard methods may be applied to synthesize a gene encoding an IFN-β mutein according to this invention. For example, the complete amino acid sequence may be used to construct a back-translated gene. A DNA oligomer containing a nucleotide sequence coding for IFN-β mutein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site directed mutagenesis or another method), the DNA sequences encoding an IFN-β mutein of this invention will be inserted into an expression vector and operatively linked to an expression control sequence appropriate for expression of the IFN-β mutein in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E.coli*, including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941. We prefer pBG311. Cate et al., "Isolation Of The Bovine And Human Genes For Mullerian Inhibiting Substance And Expression Of The Human Gene In Animal Cells", *Cell*, 45, pp. 685–98 (1986).

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

Any suitable host may be used to produce the IFN-β muteins of this invention, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E.coli, Pseudomonas, Bacillus, Streptomyces*, fungi, yeast, insect cells such as *Spodoptera frugiperda* (SF9), animal cells such as Chinese hamster ovary (CHO) and mouse cells such as NS/O, African green monkey cells such as COS 1, COS 7, BSC 1, BSC 40, and BMT 10, and human cells, as well as plant cells in tissue culture. For animal cell expression, we prefer CHO cells and COS 7 cells in cultures and particularly the CHODDUKY-B1 cell line (infra, p. 14).

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, preferred vectors for use in this invention include those that allow the DNA encoding the IFN-β muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrofolate Reductase cDNA Gene: Analysis Of Signals Utilized For Efficient Expression", *Mol. Cell. Biol.*, 2, pp. 1304–19 (1982)) or glutamine synthetase ("GS") amplification (see, e.g., U.S. Pat. No. 5,122,464 and European published application 338,841).

In selecting an expression control sequence, a variety of factors should also be considered. These include, for example, the relative strength of the sequence, its controllability, and its compatibility with the actual DNA sequence encoding the IFN-β mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters, one of skill in the art may select various vector/expression control sequence/host combinations that will express the desired DNA sequences on fermentation or in large scale animal culture, for example, using CHO cells or COS 7 cells.

The IFN-β muteins obtained according to the present invention may be glycosylated or unglycosylated depending on the host organism used to produce the mutein. If bacteria are chosen as the host then the IFN-β mutein produced will be unglycosylated. Eukaryotic cells, on the other hand, will glycosylate the IFN-β muteins, although perhaps not in the same way as native IFN-β is glycosylated.

The IFN-β mutein produced by the transformed host can be purified according to any suitable method. Various methods are known for purifying IFN-β. See, e.g., U.S. Pat. Nos. 4,289,689, 4,359,389, 4,172,071, 4,551,271, 5,244,655, 4,485,017, 4,257,938 and 4,541,952. We prefer immunoaffinity purification. See, e.g., Okamura et al., "Human Fibroblastoid Interferon: Immunosorbent Column Chromatography And N-Terminal Amino Acid Sequence", *Biochem.*, 19, pp. 3831–35 (1980).

The biological activity of the IFN-β muteins of this invention can be assayed by any suitable method known in the art. Such assays include antibody neutralization of antiviral activity, induction of protein kinase, oligoadenylate 2,5-A synthetase or phosphodiesterase activities, as described in EP-B1-41313. Such assays also include immunomodulatory assays (see, e.g., U.S. Pat. No. 4,753,795), growth inhibition assays, and measurement of binding to cells that express interferon receptors.

The IFN-β mutein of this invention will be administered at a dose approximately paralleling that employed in therapy with wild type native or recombinant IFN-β. An effective amount of the IFN-β mutein is preferably administered. An "effective amount" means an amount capable of preventing or lessening the severity or spread of the condition or indication being treated. It will be apparent to those of skill in the art that the effective amount of IFN-β mutein will depend, inter alia, upon the disease, the dose, the administration schedule of the IFN-β mutein, whether the IFN-β mutein is administered alone or in conjunction with other therapeutic agents, the serum half-life of the composition, and the general health of the patient.

The IFN-β mutein is preferably administered in a composition including a pharmaceutically acceptable carrier. "Pharmaceutically acceptable carrier" means a carrier that does not cause any untoward effect in patients to whom it is administered. Such pharmaceutically acceptable carriers are well known in the art. We prefer human serum albumin.

The IFN-β muteins of the present invention can be formulated into pharmaceutical compositions by well known methods. See, e.g., Remington's Pharmaceutical Sciences by E. W. Martin, hereby incorporated by reference, describes suitable formulations. The pharmaceutical composition of the IFN-β mutein may be formulated in a variety of forms, including liquid, gel, lyophilized, or any other suitable form. The preferred form will depend upon the particular indication being treated and will be apparent to one of skill in the art.

The IFN-β mutein pharmaceutical composition may be administered orally, intravenously, intramuscularly, intraperitoneally, intradermally or subcutaneously or in any other acceptable manner. The preferred mode of administration will depend upon the particular indication being treated and will be apparent to one of skill in the art.

The pharmaceutical composition of the IFN-β mutein may be administered in conjunction with other therapeutic agents. These agents may be incorporated as part of the same pharmaceutical composition or may be administered separately from the IFN-β mutein, either concurrently or in accordance with any other acceptable treatment schedule. In addition, the IFN-β mutein pharmaceutical composition may be used as an adjunct to other therapies.

Accordingly, this invention provides compositions and methods for treating viral infections, cancers or tumors, abnormal cell growth, or for immunomodulation in any suitable animal, preferably a mammal, most preferably human.

In order that this invention may be better understood, the following examples are set forth. These examples are for the purpose of illustration only, and are not to be construed as limiting the scope of the invention in any manner.

Examples

Expression Vector Containing Human IFN-β(phe$_{101}$)

We used plasmid pBG311 as the expression vector. A full description of pBG311 is given in Cate et al., "Isolation Of The Bovine And Human Genes For Mullerian Inhibiting Substance And Expression Of The Human Gene In Animal Cells", *Cell*, 45, pp. 685–98 (1986). The vector uses the SV40 early promoter, splice signal, and polyadenylation signal and was constructed using pAT153 as backbone.

A DNA fragment containing the DNA sequence shown in FIG. 2 (SEQ ID NO: 2) was cloned into pBG311 and operatively linked to the SV40 early promoter through a DNA sequence encoding the signal sequence for native IFN-β according to standard protocols. The resulting expression vector was designated pBeta-phe. The IFN-β mutein DNA sequence (SEQ ID NO: 2) encodes an IFN-β mutein having an amino acid sequence identical to wild type IFN-β except that the val (V) at position 101, numbered in accordance with wild type IFN-β, is substituted with phe (F). The mutein encoded by this sequence is designated IFN-β($phe_{101}$).

Competent *Escherichia coli* (SURE™, Stratagene) were transformed with the pBeta-phe plasmid according to standard procedures. Colonies containing the pBeta-phe plasmid (i.e., containing a DNA sequence encoding IFN-β($phe_{101}$) were identified by hybridization to a oligonucleotide probe specific for IFN-β($phe_{101}$) using a standard protocol (Grunstein and Hogness, 1975).

Amplification Vector

We used plasmid pAdD26SV(A)-3 to amplify the IFN-β($phe_{101}$) gene in our ultimate transformants. This plasmid is described in Kaufman and Sharp, "Construction Of A Modular Dihydrafolate Reductase cDNA Gene: Analysis Of Signals Utilized For Efficient Expression", *Mol. Cell. Biol.*, 2, pp. 1304–19 (1982) and in U.S. Pat. No. 4,740,461. The plasmid expresses murine dihydrofolate reductase (DHFR) under the transcriptional control of the Adenovirus 2 (Ad2) major late promotor (MLP). A 5' splice site, derived from an immunoglobulin variable region gene, is located between the Ad2 MLP and the DHFR coding sequences. The SV40 polyadenylation site is present downstream of the DHFR gene. The plasmid contains the prokaryotic origin of replication (ori) and tetracycline resistance gene from pBR322.

Transformation of a Cell Line

The CHO-DUKX-B1 DHFR⁻ cell line was cotransformed with the pBeta-phe plasmid and plasmid pAdD26SV(A)-3. This cell line was derived from the wild type CHO-K1 cell line by ethyl methanesulfonate and UV irradiation induced mutagenesis. See Chasin and Urlaub, "Isolation Of Chinese Hamster Cell Mutants Deficient In Dihydrofolate Reductase Activity", *Proc. Natl. Acad. Sci. USA*, 77, pp. 4216–20 (1980). Dihydrofolate reductase catalyzes the conversion of folate to tetrahydrofolate. Cells without functional DHFR require exogenous ribonucleosides and deoxyribonucleosides for growth. Inhibition of growth can be induced by methotrexate, a folate analogue, which binds to and inhibits DHFR. Titration of methotrexate can lead to methotrexate resistance by amplification of the DHFR gene. (Kaufman & Sharp, 1982). Amplification and increased expression of genes near DHFR often occurs when DHFR is amplified. Therefore, cells resistant to high levels of methotrexate often demonstrate increased specific productivity of nearby genes.

The pBeta-phe plasmid (restricted with Xmn1) and plasmid pAdD26SV(A)-3 (restricted with Stu1) were mixed in a ratio of 10:1, respectively. The DNA was transformed into CHO-DUKX-B1 DHFR⁻ cells by electroporation. Cells were plated in non-selective α+medium (α MEM base plus ribonucleosides and deoxyribonucleosides, 10% fetal bovine serum [FBS], 4 mM glutamine) and allowed to grow for 2 days. The medium was then exchanged for α⁻ medium (α MEM base without ribonucleosides and deoxyribonucleosides, 10% FBS, 4 mM glutamine)+50 nM methotrexate (MTX). The cells were removed by trypsinization and plated at ca. $8 \times 10^5$ cells/10 cm tissue culture plate. After 14 days, clones were picked and grown in 96 well tissue culture plates. One clone was expanded into a 12 well tissue culture plate and then 7 days later put into a 6 well tissue culture plate in the presence of 250 nM MTX. This clone was expanded into a T75 flask (grown in α⁻ medium+250 nM MTX) and then amplified in 750 nM MTX. A subclone was picked into a 96 well tissue culture plate, expanded into a 48 well tissue culture plate, then a 6 well tissue culture plate and then a T75 tissue culture flask.

Purification Of IFN-β($phe_{101}$)

IFN-β(phe101), produced by culturing the above subclone (or others similar to it) and then secreted into the culture medium, can be purified by immunoaffinity chromatography, substantially as described by Okamura et al., "Human Fibroblastoid Interferon: Immunosorbent Column Chromatography And N-Terminal Amino Acid Sequence", *Biochem.*, 19, pp. 3831–35 (1980).

CNer-Sepharose 4B resin (2 g, 7 ml) is prepared by suspending in 1 mM HCl. The gel is washed with 1 mM HCl for 15 min on a scintered glass filter. Anti-IFN-β mabs (such as BO2, Yamasa, Japan) are coupled to CNBr-Sepharose 4B resin by incubating in coupling buffer (100 mM $NaHCO_3$, pH 8.3, 500 mM NaCl) for 2 hours at room temperature on a rocker platform. Typically, 1–2 mg IFN-β mab per ml of resin is coupled, but this amount can be varied. The unreacted CNBr is blocked with 100 mM Tris-HCl, pH 8, 500 mM NaCl, overnight at 4° C. Alternately, the unreacted CNBr is blocked with 100 mM ethanolamine under substantially the same conditions.

The coupled resin is washed with three cycles of alternating pH. Each cycle consists of a wash with acetate buffer (100 mM, pH 4) containing 500 mM NaCl followed by a wash with Tris buffer (100 mM, pH 8) containing 500 mM NaCl.

A 1 cm×3 cm column (2.3 ml bed volume) is prepared with the coupled resin. The column is equilibrated with PBS (greater than 5 column volumes). IFN-β($phe_{101}$)-containing samples are diluted 1:3 in equilibration buffer, pH 6.8 and loaded. The load is chased with PBS, washed with 20 mM $K_2HPO_4$, 1M NaCl, pH 6.8, and eluted with 200 mM Na citrate, pH 2. The pH of the eluate was adjusted to 6 by diluting the sample with 500 mMMES, pH 6.

Characterization By Peptide Mapping

An IFN-β($phe_{101}$), mutein that had been produced and purified in a different and less preferred manner than described above was characterized by peptide mapping. A 30 μg aliquot of IFN-β($phe_{101}$) or wild type IFN-β sample was lyophilized, suspended in 200 μl of endoproteinase Lys-C digestion buffer (100 mM TRIS, pH 9, 0.5 mM EDTA), incubated for 12 hours at 22° with 1.5 μg of endoproteinase Lys-C and subjected to mapping analysis on a $C_8$ reversed phase HPLC column (0.45×25 cm). The column was developed with a 30 minute, 0–70% gradient of acetonitrile in 0.1% TFA at 1.4 mls/min. The column effluent was monitored at 214 nm. FIG. 4, Panel A shows a portion of the peptide map for IFN-β($phe_{101}$) with the arrowhead indicating the peptide TFLEEK (SEQ ID NO: 3). This peak did not occur in the peptide map for wild type IFN-β. FIG. 4, Panel B shows the corresponding region of a peptide map for wild type IFN-β with the arrowhead indicating the peptide TVLEEK (SEQ ID NO: 4). The identity of the TFLEEK and TVLEEK were verified by protein sequence analysis. We estimate that the β-$Phe_{101}$ and wild type β-IFN were greater than 98% pure. Protein concentrations were estimated from absorbance at 280 nm using an extinction coefficient of 1.5 for a 1 mg solution. In order to stabilize the proteins for biological studies, they were diluted to 4 µg/ml in PBS containing 5% FBS and 5 mM HEPES, pH 7.5

Antiviral Activity Of IFN-β(phe$_{101}$) In The CPE Assay

The preparation of IFN-β(phe$_{101}$) that was characterized by peptide mapping was analyzed in a Cytopathic Effect (CPE) assay for antiviral activity. A wild type recombinant IFN-β standard was prepared in Dulbecco's Modified Eagle Medium (DMEM), 10% FBS, 4mM glutamine at a concentration of 10,000 units/mL and stored in aliquots at −70° C. On day 1, standard, control and IFN-β$_{Phe}$ samples were diluted in DMEM, 10% FBS, 4 mM glutamine in three dilution series: i) starting at 64 units/mL followed by 2-fold dilutions, ii) starting at 12 units/mL followed by 1.5-fold dilutions, and iii) starting at 6 units/mL followed by 1.2-fold dilutions. Fifty microliters of the dilutions were then added in columns to the wells of 96-well microtiter plates. A549 cells were added to each well at $10^5$ cells/ml, 50 uL per well, in DMEM, 10% FBS, 4 mM glutamine and the cells are incubated at 37° C., 5% $CO_2$ for 15 to 20 hours.

The plate contents were shaken into a bleach bucket and 100 uL encephalomyocarditis virus (EMC virus) at appropriate dilution in media was added to each well. The virus and cells were incubated at 37° C., 5% $CO_2$ for 30 hours. The plate contents were then shaken into a bleach bucket and 0.75% crystal violet dye added to the plates. After 5 to 10 minutes, the plates were washed with distilled water and allowed to dry before being read visually.

Samples and standards were tested in duplicate on each assay plate, yielding two data points per dilution series per assay day.

IFN-β(phe$_{101}$) was tested in 14 assays in duplicate. Wild type recombinant IFN-β was used as a standard. Based on these experiments, IFN-β(phe$_{101}$) had a specific activity of $4.8 \times 10^8$ U/mg with a 95% confidence interval of $3.5–6.7 \times 10^8$. Wild type IFN-β had a specific activity of approximately $2.0 \times 10^8$ units/mg with a confidence interval of $1.6–2.5 \times 10^8$.

Analysis Of IFN-β(phe$_{101}$) For Receptor Binding

The IFN-β(phe$_{101}$) used in the CPE assay above was also analyzed for ability to bind to cells that express interferon receptors. For these studies we examined the binding of either wild type $^{125}$I-IFN-β or $^{125}$I-IFN-β(phe$_{101}$) to Daudi cells or A549 cells (FIG. 3). Carrier-free IFN-β was iodinated substantially according to the chloramine T method. Unreacted iodine was removed by size exclusion chromatography on a Superdex 75 column that was equilibrated in PBS containing 1 mg/ml bovine serum albumin. The concentration of the iodinated IFN-β was determined by the CPE assay, assuming a specific activity of $2 \times 10^8$ units/mg. Normally 5 ng (1 µL, 300,000 cpm) of iodinated IFN-β (either alone or in the presence of a 50 fold excess of non-iodinated interferon) was added to 1.7 mL eppendorf tubes in a total volume of less than 10 µL. The labelled ligand was allowed to bind alone (−) or was competed with unlabeled IFN-β(phe$_{101}$), α2-IFN (α2), γ-IFN (γ) or wild type recombinant IFN-β (WT).

Both Daudi cells and A549 cells (American Type Culture Collection) were used. The cells were suspended in DMEM/ 5% FBS at $2 \times 10^6$ cells/mL. To the samples of the IFN-β, 0.5 mL of the cell suspension was added. The tubes were mixed by inversion and incubated at ambient temperature for 45 minutes. The cells were then pelleted at 1000×g for 2 min and washed two times with 0.5 mL DMEM/10% FBS. Each wash was followed by a centrifugation step at 1000×g for 2 min. The cells were resuspended in 0.1 mL, transferred into tubes for counting and binding quantified in a Beckman gamma 407 counter.

The data suggest that the binding of IFN-β(phe$_{101}$) is very similar to that of wild type IFN-β on both cell types. Comparable amounts of wild type $^{125}$I-IFN-β and $^{125}$I-IFN-β(phe$_{101}$) were bound and competed similarly by noniodinated α-IFN, wild type IFN-β and IFN-β(phe$_{101}$). The binding was not affected by the addition of recombinant human γ-IFN.

Sequences

The following is a summary of the sequences set forth in the Sequence Listing:

SEQ ID NO:1—Amino acid sequence of IFN-β(phe$_{101}$)

SEQ ID NO:2—DNA sequence encoding IFN-β(phe$_{101}$), including DNA sequence encoding the signal sequence of native IFN-β

SEQ ID NO:3—Amino acid sequence of peptide TFLEEK.

SEQ ID NO:4—Amino acid sequence of peptide TVLEEK.

Deposits

*E.coli* K-12 containing plasmid pBeta-phe (which contains a DNA sequence encoding IFN-β(phe$_{101}$) and the native IFN-β signal sequence) has been deposited. The deposit was made in accordance with the Budapest Treaty and was deposited at the American Type Culture Collection, Rockville, Md., U.S.A. on Mar. 10, 1994. The deposit received the accession number 69584.

The foregoing description has been presented only for purposes of illustration and description. This description is not intended to limit the invention to the precise form disclosed. It is intended that the scope of the invention be defined by the claims appended hereto.

Met-Ser-Tyr-Asn-Leu-Leu-Gly-Phe-Leu-Gln-Arg-Ser-Ser-
Asn-Phe-Gln-Cys-Gln-Lys-Leu-Leu-Trp-Gln-Leu-Asn-Gly-
Arg-Leu-Glu-Tyr-Cys-Leu-Lys-Asp-Arg-Met-Asn-Phe-Asp-
Ile-Pro-Glu-Glu-Ile-Lys-Gln-Leu-Gln-Gln-Phe-Gln-Lys-
Glu-Asp-Ala-Ala-Leu-Thr-Ile-Tyr-Glu-Met-Leu-Gln-Asn-
Ile-Phe-Ala-Ile-Phe-Arg-Gln-Asp-Ser-Ser-Ser-Thr-Gly-
Trp-Asn-Glu-Thr-Ile-Val-Glu-Asn-Leu-Leu-Ala-Asn-Val-
Tyr-His-Gln-Ile-Asn-His-Leu-Lys-Thr-Phe-Leu-Glu-Glu-
Lys-Leu-Glu-Lys-Glu-Asp-Phe-Thr-Arg-Gly-Lys-Leu-Met-
Ser-Ser-Leu-His-Leu-Lys-Arg-Tyr-Tyr-Gly-Arg-Ile-Leu-
His-Tyr-Leu-Lys-Ala-Lys-Glu-Tyr-Ser-His-Cys-Ala-Trp-
Thr-Ile-Val-Arg-Val-Glu-Ile-Leu-Arg-Asn-Phe-Tyr-Phe--
Ile-Asn-Arg-Leu-Thr-Gly-Tyr-Leu-Arg-Asn (SEQ ID NO:1).

What is claimed is:

1. An IFN-β mutein wherein the val (V) at position 101 in wild type IFN-β, numbered in accordance with wild type IFN-β, is substituted with phe (F), tyr (Y), trp (W), or his (H), said mutein displaying an antiviral activity that is at least partially neutralized by antibodies to wild type IFN-β.

2. An IFN-β mutein having an amino acid sequence identical to wild type IFN-β except that the val (V) at position 101 in wild type IFN-β, numbered in accordance with wild type IFN-β, is substituted with phe (F), tyr (Y), trp (W) or his (H).

3. The IFN-β mutein according to claim 2, wherein the val (V) is substituted with phe (F).

4. The IFN-β mutein according to claim 2 having the formula:

Met-Ser-Tyr-Asn-Leu-Leu-Gly-Phe-Leu-Gln-Arg-Ser-Ser-
Asn-Phe-Gln-Cys-Gln-Lys-Leu-Leu-Trp-Gln-Leu-Asn-Gly-
Arg-Leu-Glu-Tyr-Cys-Leu-Lys-Asp-Arg-Met-Asn-Phe-Asp-
Ile-Pro-Glu-Glu-Ile-Lys-Gln-Leu-Gln-Gln-Phe-Gln-Lys-
Glu-Asp-Ala-Ala-Leu-Thr-Ile-Tyr-Glu-Met-Leu-Gln-Asn-
Ile-Phe-Ala-Ile-Phe-Arg-Gln-Asp-Ser-Ser-Ser-Thr-Gly-
Trp-Asn-Glu-Thr-Ile-Val-Glu-Asn-Leu-Leu-Ala-Asn-Val-
Tyr-His-Gln-Ile-Asn-His-Leu-Lys-Thr-Phe-Leu-Glu-Glu-
Lys-Leu-Glu-Lys-Glu-Asp-Phe-Thr-Arg-Gly-Lys-Leu-Met-
Ser-Ser-Leu-His-Leu-Lys-Arg-Tyr-Tyr-Gly-Arg-Ile-Leu-
His-Tyr-Leu-Lys-Ala-Lys-Glu-Tyr-Ser-His-Cys-Ala-Trp-
Thr-Ile-Val-Arg-Val-Glu-Ile-Leu-Arg-Asn-Phe-Tyr-Phe-
Ile-Asn-Arg-Leu-Thr-Gly-Tyr-Leu-Arg-Asn (SEQ ID NO:1).

5. A DNA sequence encoding an IFN-β mutein wherein the val (V) at position 101 in wild type IFN-β, numbered in accordance with wild type IFN-β, is substituted with phe (F), tyr (Y), trp (W), or his (H), said mutein displaying an antiviral activity that is at least partially neutralized by antibodies to wild type IFN-β.

6. A DNA sequence encoding an IFN-β mutein having an amino acid sequence identical to wild type IFN-β except that the val (V) at position 101 in wild type IFN-β, numbered in accordance with wild type IFN-β, is substituted with phe (F), tyr (Y), trp (W) or his (H).

7. The DNA sequence according to claim 6, wherein the val (V) is substituted with phe (F).

8. The DNA sequence according to claim 7 encoding an IFN-β mutein of the formula:

Met-Ser-Tyr-Asn-Leu-Leu-Gly-Phe-Leu-Gln-Arg-Ser-Ser-
Asn-Phe-Gln-Cys-Gln-Lys-Leu-Leu-Trp-Gln-Leu-Asn-Gly-
Arg-Leu-Glu-Tyr-Cys-Leu-Lys-Asp-Arg-Met-Asn-Phe-Asp-
Ile-Pro-Glu-Glu-Ile-Lys-Gln-Leu-Gln-Gln-Phe-Gln-Lys-
Glu-Asp-Ala-Ala-Leu-Thr-Ile-Tyr-Glu-Met-Leu-Gln-Asn-
Ile-Phe-Ala-Ile-Phe-Arg-Gln-Asp-Ser-Ser-Ser-Thr-Gly-
Trp-Asn-Glu-Thr-Ile-Val-Glu-Asn-Leu-Leu-Ala-Asn-Val-
Tyr-His-Gln-Ile-Asn-His-Leu-Lys-Thr-Phe-Leu-Glu-Glu-
Lys-Leu-Glu-Lys-Glu-Asp-Phe-Thr-Arg-Gly-Lys-Leu-Met-
Ser-Ser-Leu-His-Leu-Lys-Arg-Tyr-Tyr-Gly-Arg-Ile-Leu-
His-Tyr-Leu-Lys-Ala-Lys-Glu-Tyr-Ser-His-Cys-Ala-Trp-
Thr-Ile-Val-Arg-Val-Glu-Ile-Leu-Arg-Asn-Phe-Tyr-Phe-
Ile-Asn-Arg-Leu-Thr-Gly-Tyr-Leu-Arg-Asn (SEQ ID NO:1).

9. The DNA sequence according to claim 8 wherein the codon encoding the amino acid at position 101 is TTC.

10. A DNA sequence having the sequence of SEQ ID NO:2.

11. A recombinant DNA molecule characterized by the DNA sequence of any of claims 5 to 10, the sequence being operatively linked to an expression control sequence in the recombinant DNA molecule.

12. A host cell transformed with a recombinant DNA molecule of claim 11.

13. A method of producing an IFN-β mutein wherein the val (V) at position 101 in wild type IFN-β, numbered in accordance with wild type IFN-β, is substituted with Phe (F), tyr (Y), trp (W), or His (H), said mutein displaying an antiviral activity that is at least partially neutralized by antibodies to wild type IFN-β, the method comprising the steps of culturing a host cell according to claim 12 and collecting the IFN-β mutein.

14. The method according to claim 13, wherein the IFN-β mutein is encoded by a DNA sequence comprised by the formula of Sequence Id. No:2 and the host is an animal cell in culture.

15. A pharmaceutical composition comprising an antiviral, anticancer, antitumor or immunomodulation effective amount of the IFN-β mutein of any one of claims 1 to 4 and a pharmaceutically acceptable carrier.

* * * * *